(12) United States Patent
Farmache

(10) Patent No.: US 7,201,758 B2
(45) Date of Patent: Apr. 10, 2007

(54) REPAIRING PROCEDURE FOR THE TREATMENT OF SUPERFICIAL AND/OR PERFORANT VENOUS INSUFFICIENCY OF THE LOWER LIMBS BY MEANS OF THE APPLICATION OF CLIPS, STOPPERS AND/OR ARTIFICIAL VALVES

(76) Inventor: Alejandro Hector Farmache, Armada Argentina 267, Villa Nueva Guaymallen, Prov. de, Mendoza (AR) 5521

( * ) Notice: Subject to any disclaimer, the term of this patent is extended or adjusted under 35 U.S.C. 154(b) by 10 days.

(21) Appl. No.: 10/892,451

(22) Filed: Jul. 16, 2004

(65) Prior Publication Data

US 2005/0109351 A1 May 26, 2005

(30) Foreign Application Priority Data

Nov. 26, 2003 (AR) .............................. P03 01 04364

(51) Int. Cl.
*A61B 17/05* (2006.01)
*A61B 8/00* (2006.01)
*A61M 29/02* (2006.01)

(52) U.S. Cl. ...................................... 606/158; 600/454
(58) Field of Classification Search ................ 606/158; 600/454
See application file for complete search history.

(56) References Cited

U.S. PATENT DOCUMENTS

| 5,611,358 A | * | 3/1997 | Suval | 128/898 |
| 6,464,637 B1 | * | 10/2002 | Criton et al. | 600/441 |
| 6,520,975 B2 | * | 2/2003 | Branco | 606/159 |

* cited by examiner

*Primary Examiner*—Corrine McDermott
*Assistant Examiner*—Thomas Sweet
(74) *Attorney, Agent, or Firm*—Jacobson Holman PLLC (57) ABSTRACT

A repairing procedure for treating Superficial and/or Perforant Venous Insufficiency of the lower limbs, by means of the application of Clips, Stoppers and/or Artificial Valves. The procedure consists of the strategic and specific closure of different reflux levels in the internal and/or external saphenous veins and perforants veins, in an extravascular way by means of the use of titanium clips, or in endovascular way by means of the use of stoppers or artificial valves. In the case of using Artificial Valves the vascular function is reestablished.

5 Claims, 7 Drawing Sheets

REPAIRING PROCEDURE FOR THE TREATMENT OF SUPERFICIAL AND/OR PERFORANT VENOUS INSUFFICIENCY OF THE LOWER LIMBS BY MEANS OF THE APPLICATION OF CLIPS, STOPPERS AND/OR ARTIFICIAL VALVES

This invention relates to a repairing proceeding for treating Superficial and/or Perforant Venous Insufficiency of the lower limbs by means of the application of Clips, Stopper and/or Artificial Valves.

As it is known in the art, flebology is the speciality dedicated to the study, treatment and research of diseases affecting the veins of the body, especially varicose veins since they affect a 30% of the women population and a 15% of men in the western world. The prevalence of closed ulcers is of approximately a 0.3%. Reference: Phlebology Suppl 1 Vol. 14 1999 pages 1–126. There are three systems of venous circulation in the legs. Deep veins that are not visible and near the bones of the extremity carring the 90% of the blood. The superficial and visible veins that are under the skin and sub-cutaneous fat carry only the 10% of the blood. The Perforant Veins communicate the two systems abovementioned through the Aponeurosis of the leg. These perforant veins can be Direct or Indirect depending on the kind of communication they establish.

Venous Insufficiency is caused by the alteration of the functioning in the superficial valve-parietal, perforant and/or deep venous system, or in the muscle function of the peripheral pump. The blood flows backwards, reflux, increasing the venous pressure and producing dilatations, elongations and tortousness of the veins of the lower limbs and configuring the so-called "Varicose veins" and damaging the dermic and sub-dermic tissue. The latter is characterized by skin alterations, eczema and ulcerations, depending on the grade of alteration and the venous system involved. Edema is also produced (liquid retention in the interstitial space).

The surgical treatment of the venous insufficiency in the lower limbs currently consists of methods of venous removal or pulling up (saphenectomy and/or microsurgery). These methods are very cruel and are not exempted from complications. In the same way direct perforant veins are solved by closing them with big incisions, thus giving rise to the closing by endoscopic procedure (by means of a small incision inside the leg) but it is incomplete. Crossectomy is a surgery that solves the venous reflux at the level of the Arch of the Internal and/or External Saphenous Vein, but is also incomplete since it does not solve the rest of the system. There are other two methods of Non-Surgical Treatment as the Esclerotherapy, Closure and Endovascular Laser but their analysis is not the object of this filing.

In relation to the CHIVA Method created by Claude Franceschi in 1988, the same is a proceeding based on Color Ecodoppler but the same is based on the fact that a pathological vein can return to its normal size, developing surgical closures in order to reestablish the unidirectional flow in the diseased veins. In recent publications they have a 25% of Venous Thrombosis of Internal Saphenous Vein and high percentage of relapse in three years.

Thus it is an object of this invention to provide a repairing procedure for the treatment of Superficial and/or Perforant Venous Insufficiency of the lower limbs, through the application of Clips, Stoppers and/or Artificial Valves. Said procedure comprises the steps of evaluating the venous system of the lower limbs by means of color ecodoppler technique, detecting the different levels of vertical and transverse reflux; quantizing the detected levels, determining if the reflux level is located at the arch of the internal saphenous vein; if this is the case the arch must be completely dissected; closing all and each collateral; placing a first clip of titanium in the sepheno-femoral union at 0.5 cm of the same; placing a second clip below the outlet of the last collateral of the internal saphenous vein and making the resection of the venous section between both clips in order to avoid angionesis phenomena, and with more reason if there were an aneurysmatic dilation of said sector.

Titanium clips are always placed perpendicular to the larger axis of the vein, ensuring the complete closure of the vascular bore and obstructing the totality of the diameter. It must be checked that the closure is perfect, that there is no bleeding and in case of resection of part of the vein, that the ends are not short so as to avoid the release of the clips. It must be applied so as that the clip does not project towards the skin, and that the structures that do not correspond to the vein be taken.

Alternatively, in case the reflux level is located at any level of the Internal Saphenous Venous Trunk, the clip of titanium is located at the higher level of the reflux that generally coincides with the located dilation. If there is a venous aneurysm, it must be completed with resection leaving a clip above and below the resection.

On the other hand, in case of Insufficient Indirect Perforants, (Dodd 2, Dodd 1 or Subtibial de Boyd), or Insufficiency of Direct Perforants, they are closed with clips after surgery in the corresponding area, together with the higher level of the reflux of the Internal Saphenous Trunk. If the venous insufficiency were of the Cockett's Direct Perforant Veins (First, Second or Third), they are closed with clips of titanium by means of a small incision made in the internal face of the leg, with previous localization by Color Ecodoppler. The appropriate thing is done in case of Insufficiency of the Enrici's Fourth Perforant. The same procedure must be done with the Insufficiency of Indirect Extra-saphenous Perforants, that is to say those that do not have connection with the Internal or External Saphenous where the clip is applied at the higher level of the venous reflux. When there is Insufficiency of the soleo-gemelar Veins, previous localization with Color Ecoddopler, the clip is applied in its mouth in the Popliteal Vein.

In case of Relapsed Varicose Veins, the solution will be established based on the levels and localization of the venous reflux, with the same criteria that the mentioned above. The Insufficiency of Collaterals of the Internal Saphenous Vein, as sole presence, can take a clip at the higher level of the reflux but sometimes it is convenient to complete with resection of the vein with microincisions.

A further object of this invention is providing a procedure for the application of stoppers in lower limbs presenting superficial venous insufficiency, in which the procedure comprises the steps of performing an evaluation of the vein system of the lower limbs by means of the color ecodoppler technique; applying local anesthesia in the zone to be treated; making an incision and introducing a metallic guide inside the external or internal saphena vein in which head a Goretex stopper is placed; determining the exact diameter of the vein in order to introduce the stopper annulling in this way the reflux; locating the Goretex stopper or similar material at the higher level of reflux of the Internal and/or External Saphenous Vein, placing it so as to completely occlude the vascular bore, making impossible its movement and eliminating the reflux; controlling the previous steps by means of a color ecodoppler technique; removing the metallic guide and closing the incision. An anchoring thread for fixation is left and the same is removed after 10 days. The stopper remains in a permanent way in the vascular bore in the place where the venous flow was initiated.

Thus an object of this invention is providing a procedure for the application of an artificial valve in lower limbs presenting superficial venous insufficiency, where the procedure comprises the steps of evaluating the venous system of the lower limbs by means of color ecodoppler technique; making a small incision in the internal or external saphena vein by using a special applier, such as metallic guide, inserting an artificial guide; controlling the location of said valve by means of color ecodoppler; verifying the correct functioning by manual compression and decompression of the calf; removing the applier and closing the incision.

For a better understanding of the object of this invention, it has been illustrated in several figures in which the preferred embodiments have been represented as follows.

Figure 1:
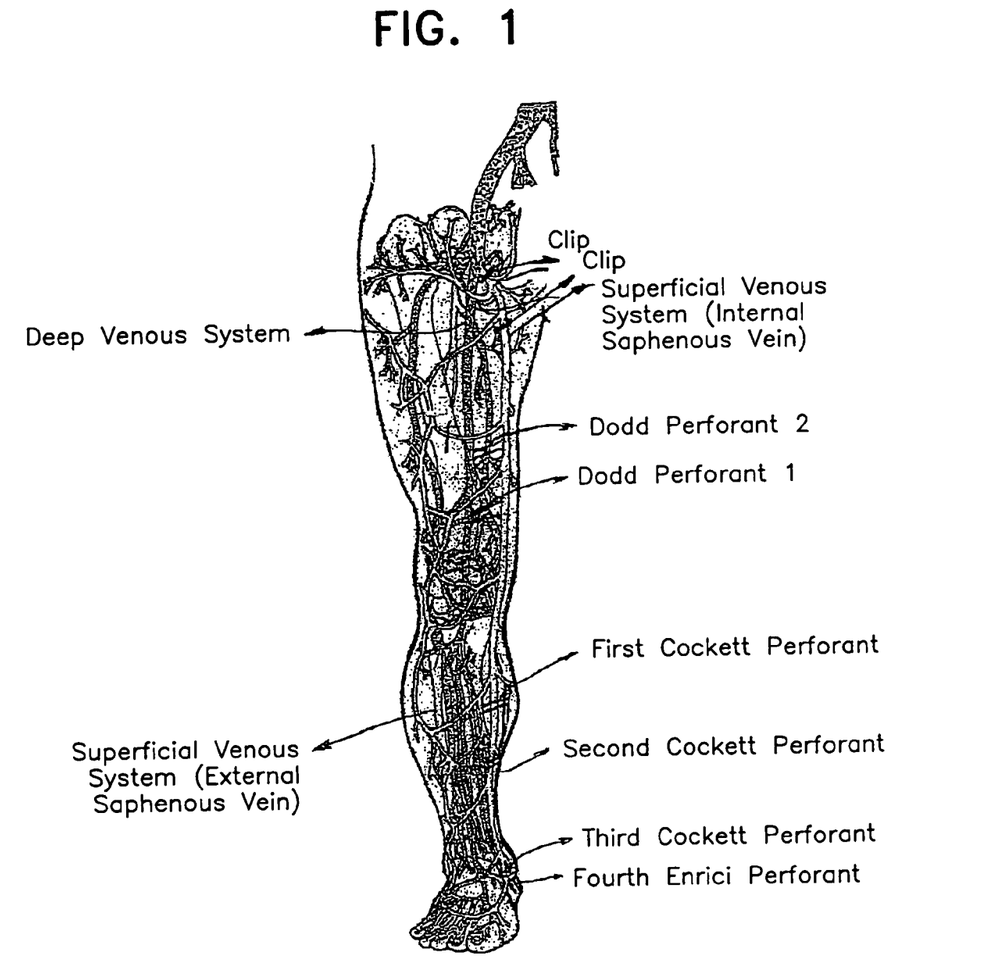
FIG. 1 is a scheme of an embodiment of the procedure object of this invention.

Referring to FIG. 1 it is observed a scheme of the Venous System of the Lower Limbs where the Superficial Venous System appears represented by the Internal and External Saphenous Veins, the Perforant Venous System and the Deep Venous System.

It is important to point out that in FIGS. 1, 2, 3 and 4 the same reference numbers were used to indicate the same parts.

In effect, in FIG. 1 the procedure for the treatment of Venous Insufficiency is illustrated, using in this particular case titanium clips or staples.

This procedure comprises the steps of evaluating the Venous System of the Lower Limbs by means of Color Ecodoppler technique. This technique consists of the use of an Ultrasonic Equipment with Doppler effect that detects the anatomic and functional characteristics of the Venous System through the Color Flow. The Doppler effect consists of a computer analysis of the frequency changes of a sound wave when bounces against a body or liquid mass in motion. It has been proved that an Ultrasonic ray can be reflected against the elements of the blood (red globules) allowing the spectral analysis of the blood flow. Further, anatomic images con be obtained according to the greater or lower density of the tissues that the ultrasonic ray encounters. The greater the density of the tissue, greater is the absorption of the sound and it is reflected in the image obtained.

By using Color Ecodoppler, the different levels of vertical and transverse flow are detected and then the levels detected are quantified and it is determined if the flow level is located in the arch of the Internal Saphenous Vein. If that is the case, as shown in FIG. 1, the arch is completely dissected, each and all the collaterals are closed with material of surgical suture, a titanium clip is applied at the site of Sapheno-femoral junction, at 0.5 cm of the same, and another clip below the mouth of the last collateral of the Internal Saphenous Vein. Thus the venous part between both clips is dried.

Figure 2:
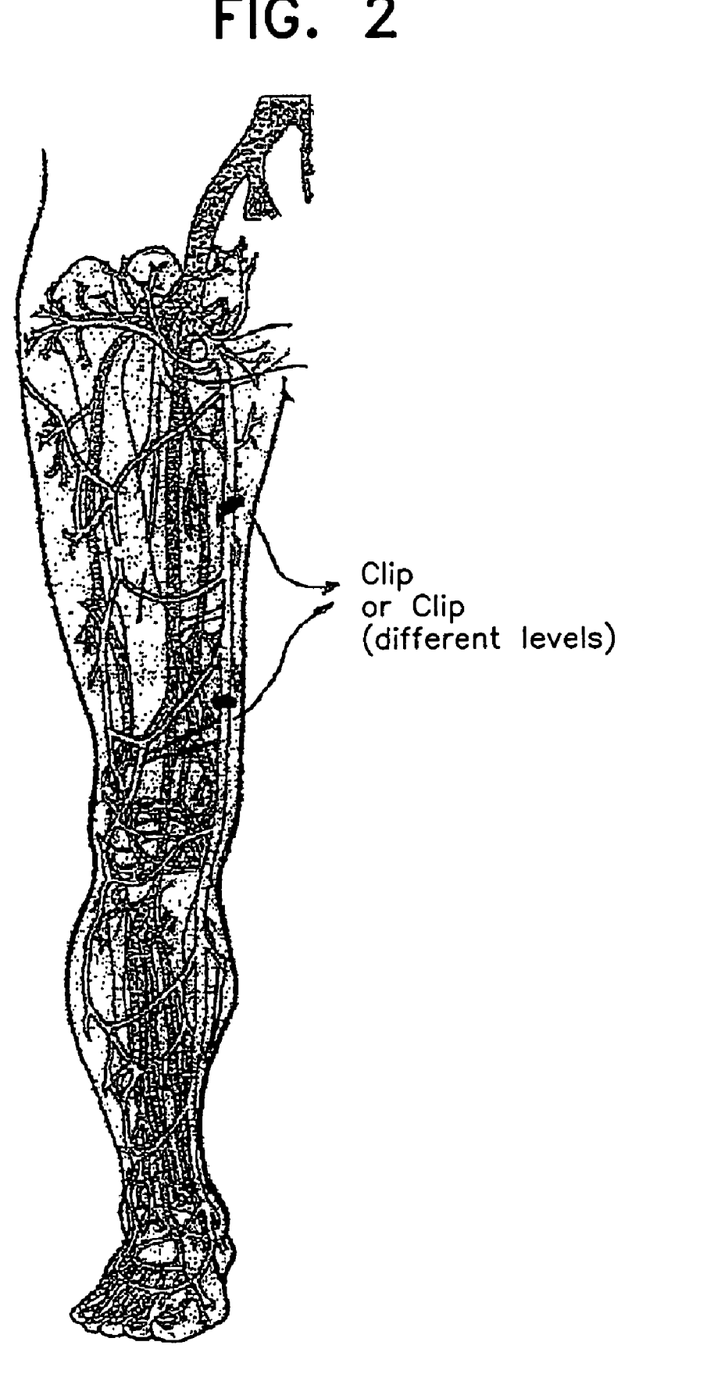
FIG. 2 is a scheme of a second embodiment of the procedure of this invention.

Alternatively, as shown in FIG. 2, in case the reflux level is located in different levels of the saphenous trunk, a clip must be placed at the higher reflux level with the technique and cares mentioned above in this presentation.

Figure 3:
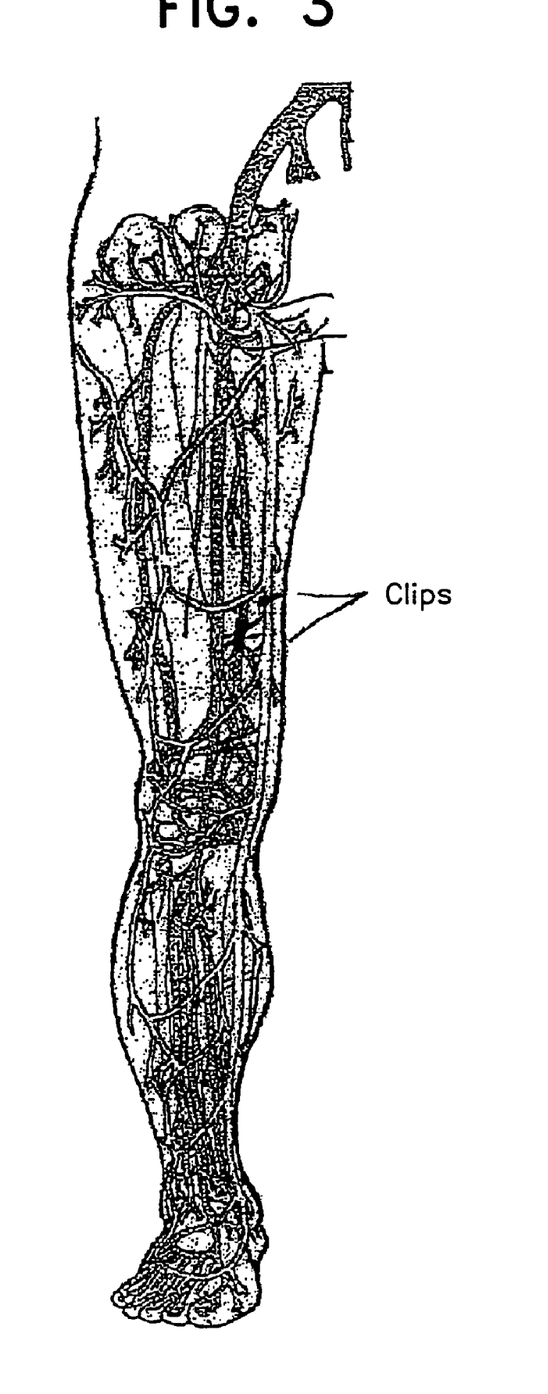
FIG. 3 is a scheme of a third embodiment of the procedure of this invention.

In FIG. 3, the placing of the clip in the Insufficient Perforant, i.e. in the one the pathologic reflux by Color Ecodoppler was detected and another clip is applied in the insufficient internal saphenous trunk, over the mouth of the Perforant in the Internal Saphenous Vein, provided that the section nearby of the internal saphenous is not compromised, in other words, reflux is not observed. Otherwise, the closing with clips of the perforant will be accompanied with the procedure of FIG. 1.

Figure 4:
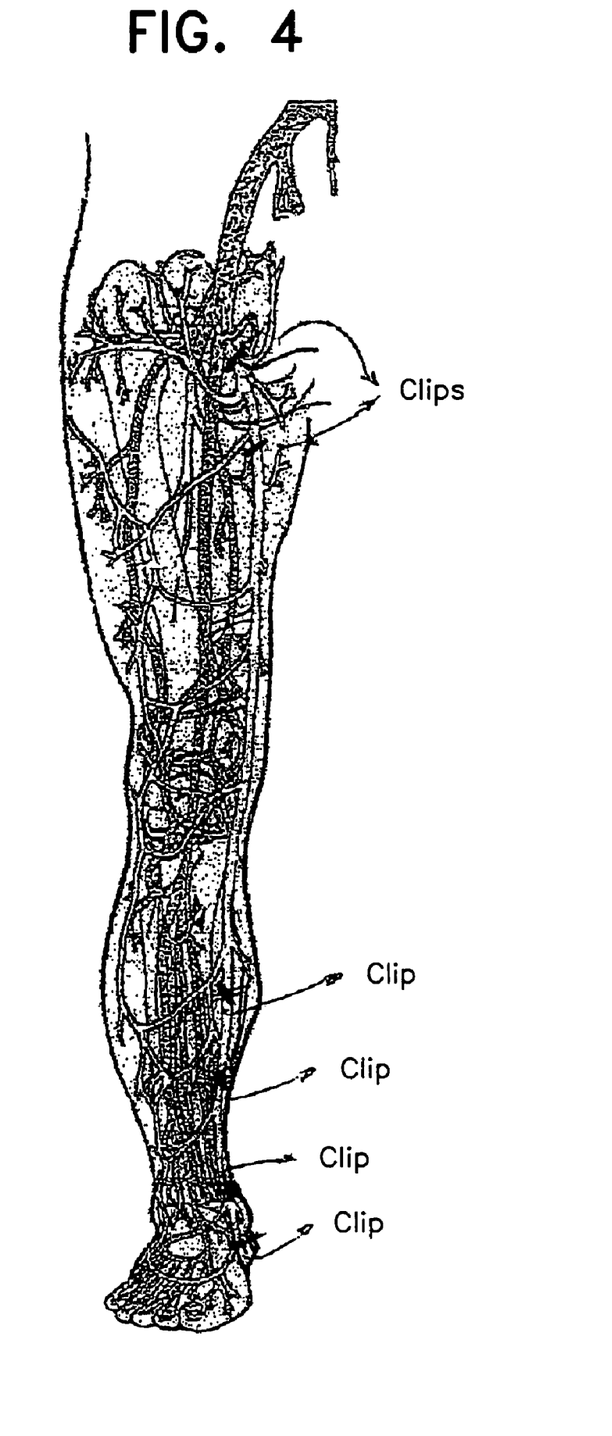
FIG. 4 is a scheme of a fourth embodiment of the procedure of this invention.

In FIG. 4 is shown the closure with titanium clips of the Direct Perforant of First, Second and Third Cockett, after detecting the insufficiency by Color Ecodoppler. In each case the technique and recommendations explained above for the application of the clips have been pointed out in the previous paragraphs of this filing.

Figure 5:
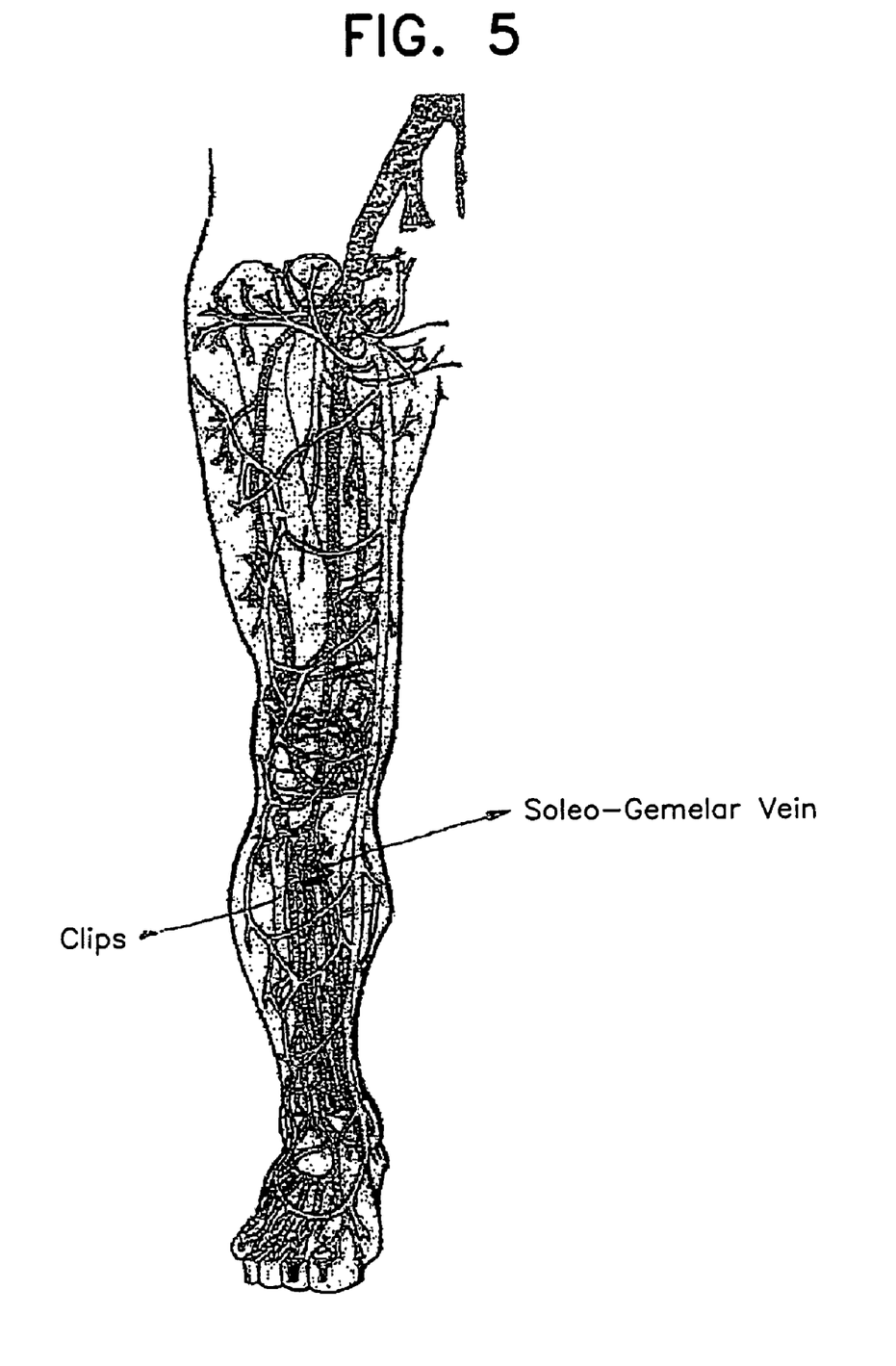
FIG. 5 is a scheme of a fifth embodiment of the procedure of this invention.

In FIG. 5 is shown the placing of the clip of titanium in the soleo-gemelar Veins in the mouth in the Popliteal Vein.

Figure 6:
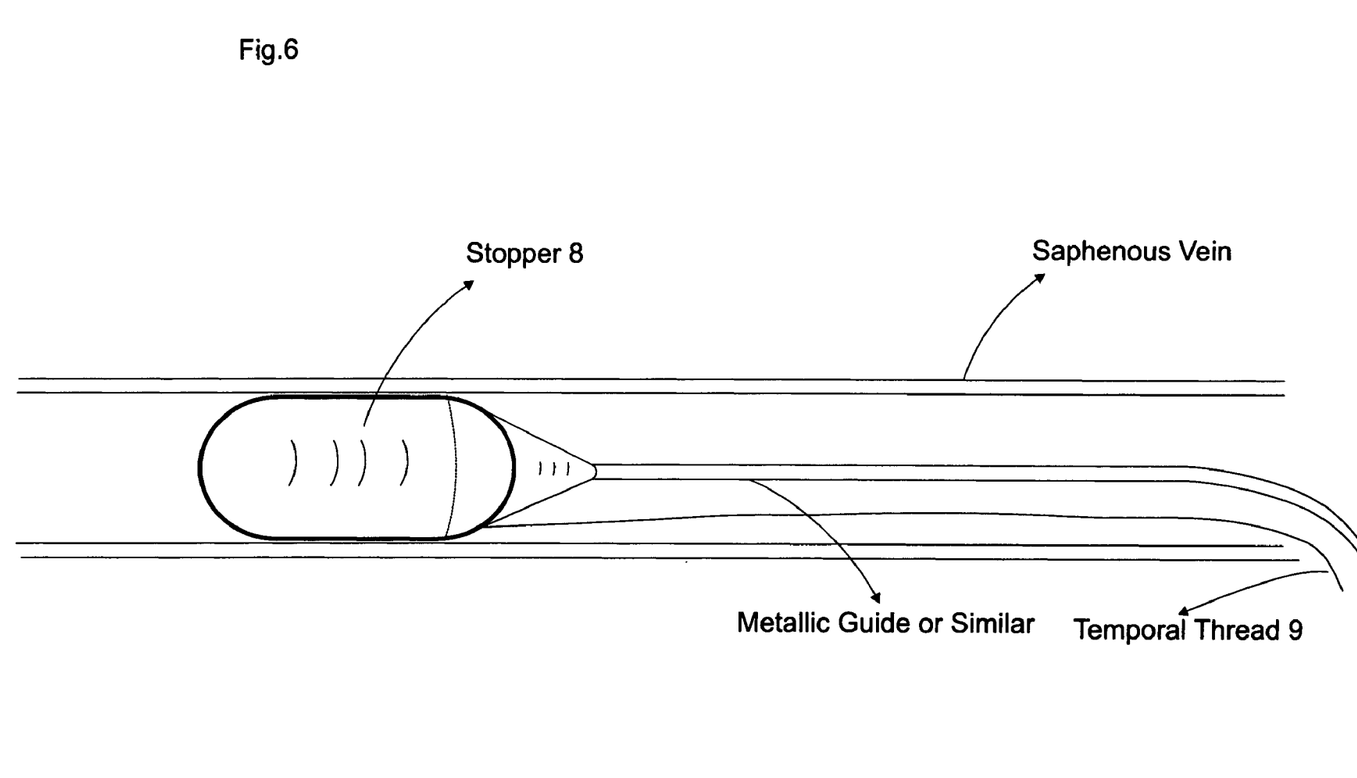
FIG. 6 is a scheme of a sixth embodiment of the procedure of this invention.

Referring to FIG. 6, it is shown the procedure for applying a stopper 8 in the Superficial Venous System 1. It is important to point out that in this particular embodiment the stopper 8 is made of reinforced PTFE, but the same can be replaced by other type of stopper fulfilling the same qualities required for this procedure.

In effect the procedure comprises the steps of evaluating the venous system of the lower limbs by means of Color Ecodoppler technique, as mentioned above. After that local anesthesia is applied in the zone to be treated and an incision is made in the Internal or External Saphenous Vein.

Later, a metallic guide is inserted inside the Internal or External Saphenous Vein in which head a Goretex stopper is applied and the exact diameter of said vein is determined in order to apply the corresponding stopper made of reinforced PTFE 8. This causes the reflux annulment. The stopper thus remains fixed at the highest level of reflux, anchored by means of a temporal thread 9 that is removed after 10 days. The stopper remains occluding the bore in a permanent way, and it will not be removed. The purpose of this thread 9 is that the stopper 8 can be fixed in a permanent way to the vascular bore. Thus stopper 8 remains occluding the vascular bore in a definite way. After the localization of the stopper in the specific place, the former steps must be controlled again through Color Ecodoppler technique, the metallic guide is removed and the incision is closed, allowing the patient to go home without pain.

Figure 7:
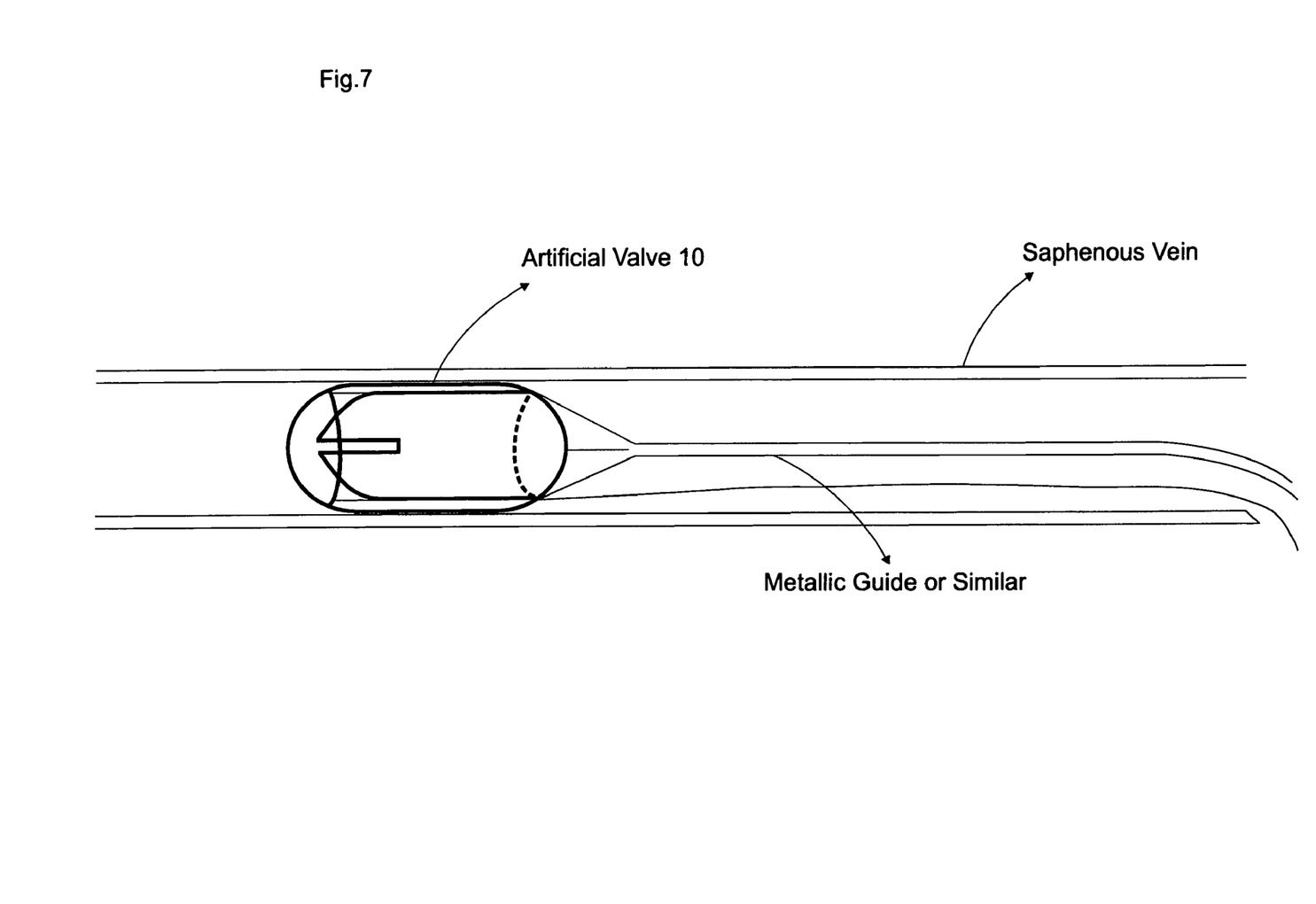
FIG. 7 is a scheme of a seventh embodiment of the procedure of this invention.

Referring to FIG. 7, a third alternative for carrying out the procedure object of this invention is observed, where in this particular case an artificial valve 10 is used. It is important to mention that the artificial valve 10 defines a restoration of the venous functionality to the return flow and the flow in the veins is eliminated.

In effect, the procedure is quite similar to the procedure explained before in relation to stoppler 8 of FIG. 6 where also an evaluation is performed in connection with the venous system of the inferior limbs by means of Color Ecodoppler technique. After that a small incision is made after local anesthesia, in the External or Internal Saphenous Vein. By means of the use of a special applier, such as a metallic guide, the artificial valve 10 is introduced. Then, the location of said valve is checked by means of Color Ecodoppler, verifying the correct functioning of the same by manual compression and decompression of the calf. Then the metallic applier is removed and the small incisional gap made for inserting the artificial valve 10 mentioned above is closed.

It is important to mention that in this particular embodiment an artificial valve 10 of antiallergenic material has been used since it does not cause rejection once inserted. Further, when inserting the valve it is convenient to use heparin of low molecular weight in prophylactic doses with the purpose of reducing the thrombogenic capacity.

It is important to point out that the procedures exposed in this filing have a concept of systematic, strategic, specific and complete order since the purpose is to repair the different levels of venous affectation, modifying the physiopatologic alterations and eliminating the concept of extirpation and extraction. Besides, leaving parts of the External or Internal Saphenous Vein viable for future surgical uses of coronary or peripheral by-pass, give more importance to the procedures mentioned herewith.

What is claimed is:

1. A repairing procedure for the treatment of superficial and/or perforant venous insufficiency of the lower limbs by means of the application of clips, wherein this procedure comprises the following steps:
   a) evaluating the venous system of lower limbs by means of an ultrasonic equipment with color doppler effect;
   b) detecting different levels of vertical and transverse reflux;
   c) quantifying the levels detected;
   d) verifying that the reflux level is located at the arch of the internal saphenous vein;
   e) dissecting the arch; closing each and all collaterals; placing a first clip in the sapheno-femoral junction; and placing a second clip below the mouth of the last collateral of the internal saphenous vein;
   f) verifying that the reflux level is located at different levels of the trunk;
   g) placing a clip at a higher level of the reflux;
   h) resectioning a venous aneurysm by placing a clip over and below the resection;
   i) placing a clip in order to close an indirect or direct perforant vein where the reflux is located, during surgical procedure in a corresponding area; and
   i) the venous part between both clips in step e) is extirpated.

2. The procedure according to claim 1, wherein said first and second clips are placed perpendicularly to a larger axis of the vein.

3. The procedure according to claim 1, wherein the placing of said clips defines a complete obstruction of a vascular bore.

4. The procedure according to claim 1, wherein said procedure further comprising the following steps:
   j) verifying the perfect closure of the vein;
   k) verifying that there is no bleeding;
   l) in case of resection of the vein, verifying that the ends of the vein are not too short so as to allow the release of the clips;
   m) the placing of the clips must be done taking into account that the clips are not projected toward skin; and
   n) avoiding placing the clips to take structures that do not correspond to the vein.

5. The procedure according to claim 1, wherein said clips are made of titanium.

* * * * *